United States Patent
Pang

(10) Patent No.: US 10,905,675 B2
(45) Date of Patent: Feb. 2, 2021

(54) USE OF CARBAMATE COMPOUND FOR PREVENTION, ALLEVIATION OR TREATMENT OF PRURITUS

(71) Applicant: SK BIOPHARMACEUTICALS CO., LTD., Gyeonggi-do (KR)

(72) Inventor: Min Hee Pang, Gyeonggi-do (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 0 days.

(21) Appl. No.: 16/468,788

(22) PCT Filed: Dec. 14, 2017

(86) PCT No.: PCT/KR2017/014733
§ 371 (c)(1),
(2) Date: Jun. 12, 2019

(87) PCT Pub. No.: WO2018/111003
PCT Pub. Date: Jun. 21, 2018

(65) Prior Publication Data
US 2020/0069645 A1 Mar. 5, 2020

(30) Foreign Application Priority Data
Dec. 14, 2016 (KR) .................. 10-2016-0170227

(51) Int. Cl.
*A61K 31/41* (2006.01)
*A61P 17/04* (2006.01)
(52) U.S. Cl.
CPC .............. *A61K 31/41* (2013.01); *A61P 17/04* (2018.01)
(58) Field of Classification Search
CPC ................................ A61K 31/41; A61P 17/04
USPC ........................................................ 514/381
See application file for complete search history.

(56) References Cited

U.S. PATENT DOCUMENTS

| 2006/0258718 | A1* | 11/2006 | Choi | ....................... | A61P 25/30 |
| | | | | | 514/359 |
| 2007/0129400 | A1 | 6/2007 | Duan et al. | | |
| 2013/0079313 | A1 | 3/2013 | Armani et al. | | |

FOREIGN PATENT DOCUMENTS

| KR | 10-2008-0005437 A | 1/2008 |
| KR | 10-2009-0088442 A | 8/2009 |
| KR | 10-2014-0090984 A | 7/2014 |
| WO | WO-2006/112685 A1 | 10/2006 |
| WO | WO-2010/150946 A1 | 12/2010 |
| WO | WO-2011/046380 A2 | 4/2011 |
| WO | WO-2013/048214 A2 | 4/2013 |

OTHER PUBLICATIONS

Extended European Search Report from corresponding European Patent Application No. 17880053.8, dated May 18, 2020.
Leibel, F., et al.; "Anti-inflammatory and anti-itch activity of sertaconazole nitrate", Arch Dermatol Res (2006), 298, pp. 191-199.
Grundmann et al, Chronic pruritus: Clinics and treatment, Ann Dermatol, 2011.
Dalgard et al, Self-reported skin morbidity in Oslo: Associations with sociodemographic factors among adults in a cross-sectional study. Br J Dermatol, 2004.
Ikoma et al, The neurobiology of itch, Nature Reviews Neuroscience, 2006.
Wolkenstein et al, French people and skin diseases: results of a survey using a representative sample. Arch Dermatol, 2003.
Matterne et al, Prevalence, correlates and characteristics of chronic pruritus: a population-based cross-sectional study. Acto Derm Venereol, 2011.
Yosipovitch et al, Chronic pruritus, the new England journal of medicine, 2013.
Patel et al, Therapy of pruritus, Expert Opinion of Pharmacotherapy. 2010.
Stander et al, Clinical Classification of Itch: a Position Paper of the International Forum for the Study of Itch, Acta Derm Venereol 2007).
Back et al, Chronically relapsing pruritic dermatitis in the rats treated as neonate with capsaicin; a potential rat model of human atopic dermatitis, Journal of Derm Science, 2012.
International Search Report from corresponding PCT Application No. PCT/KR2017/014733, dated Mar. 20, 2018, with English translation.

* cited by examiner

*Primary Examiner* — Yevgeny Valenrod
(74) *Attorney, Agent, or Firm* — Harness, Dickey & Pierce, P.L.C.

(57) ABSTRACT

The present invention relates to a use for preventing, alleviating or treating pruritus by administering a pharmaceutical composition comprising a carbamate compound of following Formula 1.

12 Claims, 2 Drawing Sheets

USE OF CARBAMATE COMPOUND FOR PREVENTION, ALLEVIATION OR TREATMENT OF PRURITUS

CROSS-REFERENCE TO RELATED APPLICATIONS

This application is a national phase application of PCT Application No. PCT/KR2017/014733, filed on Dec. 14, 2017, which claims the benefit and priority to Korean Patent Application No. 10-2016-0170227, filed on Dec. 14, 2016. The entire disclosures of the applications identified in this paragraph are incorporated herein by references.

FIELD

The present invention relates to use of a carbamate compound of the following Formula 1 for the purpose of preventing, alleviating or treating pruritus by administering a pharmaceutical composition comprising said carbamate compound:

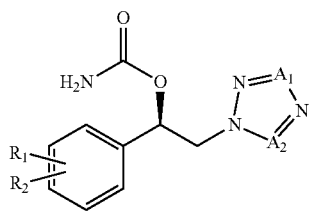

[Formula 1]

wherein,
$R_1$, $R_2$, $A_1$ and $A_2$ are as defined herein.

BACKGROUND

Pruritus (or itching) is defined as an unpleasant sensation causing an impulse (urge) to scratch or rub the skin. Pruritus is not only a typical symptom of various skin diseases, but it is also a relatively common symptom that can occur even in the case of systemic disease throughout the body, which acts as a serious detriment to the quality of life (Grundmann et al, Chronic pruritus: Clinics and treatment, Ann Dermatol, 2011; Ikoma et al, The neurobiology of itch, Nature Reviews Neuroscience, 2006).

It has been reported in an overseas study that the incidence of pruritus was 8.4% in the general population and 42% in patients with skin disease. However, due to the heterogeneity of the etiology and the patient population, it has not yet been accurately accounted for in Korea (Dalgard et al, Self-reported skin morbidity in Oslo: Associations with sociodemographic factors among adults in a cross-sectional study. Br J Dermatol, 2004; Wolkenstein et al, French people and skin diseases: results of a survey using a representative sample. Arch Dermatol, 2003). Pruritus causes the patient to scratch, resulting in skin damage, increased risk of skin infection, and aggravation of skin inflammation. However, despite the manifestation of such clinically significant symptoms, the mechanism of onset of pruritus is not well known, and options for its treatment are limited (Paus, R., et al., J. Clin. Invest. 2006, 116: 1174-1185).

Pruritus may occur in the form of acute pruritus or chronic pruritus, and chronic pruritus is defined as the case where an itchy sensation is maintained for more than 6 weeks (Matterne et al, Prevalence, correlates and characteristics of chronic pruritus: a population-based cross-sectional study. Acto Derm Venereol, 2011). The pathological mechanism of acute and chronic pruritus has not been fully understood until now, but it is predicted that the main cause is the over-activation of the neurotransmission pathway which detects the itching signal due to contact with an external substance, the change of ambient temperature, stimulation by a chemical substance or electric stimulation and the like. It is known that the itching signal is recognized in the unmyelinated C-fiber under the epidermis and transmitted through the lateral spinothalamic tract to the thalamus and sensory cortex in the brain, thereby finally being perceived as an itchy feeling. And it is presumed that abnormalities of various itch-mediators and pruriceptors (itch-sensing receptors) acting on these neurotransmission pathways cause excessive pruritus (Ikoma et al, The neurobiology of itch, Nature Reviews Neuroscience, 2006; Yosipovitch et al, Chronic pruritus, The new England journal of medicine, 2013).

For the treatment of pruritus, medication is mainly used, and steroids and antihistamine drugs are the most widely used, but they are known to have some level of side effects. When the above drugs are not effective, itch-mediator inhibitors, anticonvulsants, antidepressants, opioid antagonists, immuno-suppressants and the like may be used for the treatment of pruritus depending on the etiology, mechanism and symptoms. In addition thereto, mild cleansers, emollients, coolants or topical anesthetics are also known to be helpful as adjunctive symptom relief measures (Patel et al, Therapy of pruritus, Expert Opinion of Pharmacotherapy. 2010; Yosipovitch et al, Chronic pruritus, The new England journal of medicine, 2013).

As such, a variety of pharmacological therapies have been used for the treatment of pruritus, but there are still limitations in their use due to an unsatisfactory level of effect or side effects. Hence, there is still a need for new drugs with improved efficacy and fewer side effects.

DISCLOSURE

Problem to be Solved

The present invention is intended to provide a method for the prevention, alleviation or treatment of pruritus (itching).

The present invention is also intended to provide the use of a carbamate compound of the following Formula 1, or a pharmaceutically acceptable salt, solvate or hydrate thereof, for the prevention, alleviation or treatment of pruritus:

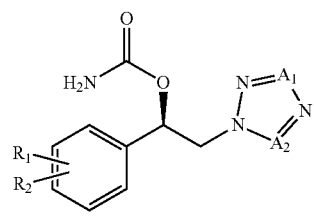

[Formula 1]

wherein,
$R_1$, $R_2$, $A_1$ and $A_2$ are as defined herein.

Technical Solution to the Problem

The present invention provides a medicament for the prevention, alleviation or treatment of pruritus, comprising a therapeutically effective amount of a carbamate compound of the following Formula 1, or a pharmaceutically acceptable salt, solvate or hydrate thereof:

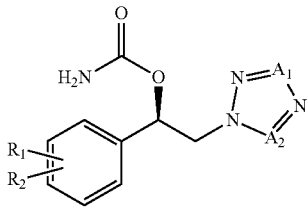

[Formula 1]

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

In addition, the present invention provides a pharmaceutical composition for the prevention, alleviation or treatment of pruritus, comprising a therapeutically effective amount of the carbamate compounds of the above Formula 1, or a pharmaceutically acceptable salt, solvate or hydrate thereof, and further one or more of a pharmaceutically acceptable carrier.

In addition, the present invention provides a method for preventing, alleviating or treating pruritus in a subject, comprising administering to the subject a therapeutically effective amount of the carbamate compounds of the above Formula 1, or a pharmaceutically acceptable salt, solvate or hydrate thereof.

In addition, the present invention provides the use of the carbamate compounds of the above Formula 1, or a pharmaceutically acceptable salt, solvate or hydrate thereof for the prevention, alleviation or treatment of pruritus, or for the improvement of symptoms associated with pruritus.

In one embodiment of the present invention, in the above Formula 1, $R_1$ and $R_2$ are each independently selected from the group consisting of hydrogen, halogen $C_1$-$C_8$ alkyl.

In one embodiment, the halo $C_1$-$C_8$ alkyl is perfluoroalkyl.

According to another embodiment of the present invention, the carbamate compound of the above Formula 1 is carbamic acid (R)-1-(2-chlorophenyl)-2-tetrazol-2-yl)ethyl ester of the following Formula 2:

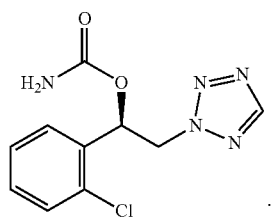

[Formula 2]

A person having ordinary skill in the art of synthesis of compounds could have easily prepared the carbamate compounds of the above Formulas 1 and 2 using known compounds or compounds which can be easily prepared therefrom. In particular, methods for preparing the compounds of the above Formula 1 are described in detail in PCT Publication Nos. WO 2006/112685 A1, WO 2010/150946 A1 and WO 2011/046380 A2, the disclosures of which are incorporated herein by reference. The compounds of the above Formula 1 can be chemically synthesized by any of the methods described in the above documents, but the methods are merely exemplary ones, and the order of the unit operation and the like may be selectively changed if necessary. Hence, the above methods are not intended to limit the scope of the invention.

The carbamate compounds of the above Formula 1 can be used for the prevention, alleviation or treatment of pruritus (itching).

As used herein, the term "pruritus (or itching)" refers to a sensation that causes a reflex reaction to scratch or rub the skin. Pruritus may be a symptom of a disease, disorder or infection and may occur spontaneously without underlying or identifiable physiological causes (idiopathic pruritus). Pruritus includes all types of acute, intermittent or persistent, local or systemic itching and stinging sensations. Pruritus may also be idiopathic, allergic, metabolic, infectious, drug-induced, or due to liver or kidney disease or cancer.

According to one embodiment of the present invention, the pruritus may be an acute pruritus.

According to one embodiment, the acute pruritus may be acute pruritus due to skin disease.

According to one embodiment, the acute pruritus may be caused by one or more selected from Erythema multiforme, Urticaria caused by external allergens (allergy-inducing substances) and Acute eczematous dermatitis.

According to one embodiment of the present invention, the pruritus may be a chronic pruritus.

According to one embodiment, the chronic pruritus may be one or more selected from chronic pruritus caused by skin diseases (Dermatological itch), pruritus caused by systemic diseases (Systemic itch), pruritus caused by neuropathies (Neuropathic itch), pruritus caused by psychotic diseases (Psychogenic itch) and mixed-type pruritus thereof.

According to one embodiment, the above chronic pruritus caused by skin diseases (Dermatological itch) may be caused by one or more selected from Psoriasis, Atopic dermatitis, Contact dermatitis, Urticaria, Dry skin, Prurigo, Scabies mite, Insect bite, Mycotic, bacterial and viral infections, Folliculitis, Pediculosis, Bullous dermatoses, Dermatitis herpetiformis Duhring, Bullous pemphigoid, Dermatomyositis, Darier's disease (Keratosis follicularis), Hailey-Hailey disease (Chronic pemphigus), Ichthyosis, Sjogren-Larsson syndrome, Epidermolysis bullosa pruriginosa, Polymorphic eruption of pregnancy, Pemphigoid gestationis, Prurigo gestationis, Cutaneous T-cell and B-cell lymphoma and Leukemic infiltrates of the skin.

According to one embodiment, the above pruritus caused by systemic diseases (Systemic itch) may be caused by one or more selected from Chronic liver disease, Chronic renal failure, Diabetes mellitus, Biliary Atresia, Uremia, Hyperthyroidism, Malabsorption, Perimenopausal pruritus, HIV infection, Helminthiasis, Iron deficiency, Polycythaemia vera, Hodgkin's disease, Non-Hodgkin's lymphoma, Plasmocytoma, Solid tumours of the cervix, prostate or colon, Carcinoid syndrome, Pruritus gravidarum, and administration of drugs such as Opioids, ACE inhibitors (angiotension converting enzyme inhibitors), Amiodarone, Hydrochlorothiazide, Estrogens, Simvastatin, Hydroxyethyl starch and Allopurinol.

According to one embodiment, the above pruritus caused by neuropathies (Neuropathic itch) may be caused by one or more selected from Post-herpetic pruritus, Notalgia paresthetica, Brachioradial pruritus, Post-cerebrovascular accident (CVA) pruritus (Post-stroke pruritus), Multiple sclerosis, Neoplasms (especially tumor), Abscesses, Cerebral or spinal infarcts, Vulvodynia and Small fiber neuropathy.

According to one embodiment, the above pruritus caused by psychotic diseases (Psychogenic itch) may be caused by one or more selected from Delusions of parasitosis, Stress, Depression, Anxiety disorders, Obsessive-compulsive disorders, Schizophrenia, Tactile hallucinosis and Systemic fatigue.

According to one embodiment, the above mixed-type pruritus refers to a case where itching is caused by the simultaneous occurrence of some of the aforementioned diseases (Ikoma et al, The neurobiology of icth, Nature Reviews Neuroscience, 2006; Stander et al, Clinical Classification of Itch: a Position Paper of the International Forum for the Study of Itch, Acta Derm Venereol 2007).

In one embodiment, animal models may be particularly useful in analyzing the efficacy of potential anti-pruritic agents. For example, animal pruritus models can be used to determine the in vivo efficacy of histamine receptor (H3) antagonists. In one embodiment, the evaluation of the pruritus model is based on the behavior of the animal (behaviorally based).

A pruritus model refers to an in vivo or in vitro model system representing at least one aspect or factor of itching, and it allows evaluation of anti-itching agents. In one embodiment, the pruritus model has a mammalian origin. In one embodiment, the pruritus model can be selected from a pruritogen (a pruritus-inducing substance such as serotonin) injection model, a passive cutaneous anaphylaxis model, an allergic pruritus model, and a spontaneous pruritus model.

In the pruritogen injection model, pruritus may be caused by an intradermal or subcutaneous injection into the rostral part of the back of a mouse or rat of a pruritogen such as histamine, serotonin, substance P, chloroquine, protease-activated receptor 2 (PAR-2) activating peptide and trypsin. After injection of the pruritogen, the animals are recorded in video and the number of times the injection site is scraped with the hind legs is measured. The test compound may be administered orally or by other routes immediately before induction of pruritus, and the efficacy of the test compound may be compared to the positive control compound.

The dosage of the carbamate compounds of Formula 1 for the prevention, alleviation or treatment of the above diseases may typically vary depending on the severity of the disease, the body weight and the metabolic status of the subject. A "therapeutically effective amount" for an individual patient refers to an amount of the active compound sufficient to achieve the above pharmacological effect, i.e., the therapeutic effect as described above. The therapeutically effective amount of the compounds of Formula 1 is 50 to 500 mg, 50 to 400 mg, 50 to 300 mg, 100 to 400 mg, 100 to 300 mg, 50 to 200 mg, or 100 to 200 mg, based on the free form and once-daily administration to humans. The therapeutically effective amount is preferably 50 to 300 mg, more preferably 50 to 200 mg.

The compounds of the present invention may be administered by any conventional method used for administration of a therapeutic agent, such as oral, parenteral, intravenous, intramuscular, subcutaneous or rectal administration.

The medicament or pharmaceutical composition according to one embodiment of the present invention may comprise a therapeutically effective amount of a compound selected from the group consisting of the carbamate compounds of the present invention, their pharmaceutically acceptable salts, solvates, hydrates and combinations thereof.

Examples of the pharmaceutically acceptable salts of the carbamate compounds of the above Formula 1 include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate, hydravamine, hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemisuccinate, sulfate or hemi-sulfate, tannate, tartrate, oxalate or hemi-tartrate, teoclate, triethiodide, benzathine, chloroprocaine, choline, diethanolamine, ethylenediamine, meglumine, procaine, aluminum, ammonium, tetramethylammonium, calcium, lithium, magnesium, potassium, sodium and zinc.

The medicament or pharmaceutical composition according to one embodiment of the present invention may be administered orally or parenterally. The parenteral administration may include intravenous injection, subcutaneous injection, intramuscular injection, intraperitoneal injection, endothelial administration, topical administration, intranasal administration, intravaginal administration, intrapulmonary administration, rectal administration and the like. In the case of oral administration, the pharmaceutical composition according to one embodiment of the present invention may be formulated as a plain tablet (uncoated tablet) or such that the active agent is coated or it is protected against degradation in the stomach. In addition, the composition can be administered by any device capable of transferring the active substance to a target cell. The route of administration may vary depending upon the general condition and age of the subject to be treated, the nature of the treatment condition and the active ingredient selected.

A suitable dosage of the medicament or pharmaceutical composition according to one embodiment of the present invention may vary depending on factors such as the formulation method, administration method, age, body weight and gender of patients, pathological condition, diet, administration time, administration route, excretion rate and reaction sensitivity, and doctors having ordinary skill can easily determine and prescribe dosages that are effective for the desired treatment or prophylaxis. The pharmaceutical composition according to one embodiment may be administered in one or more doses, for example, one to four times per day. The pharmaceutical composition according to one embodiment may contain the compounds of Formula 1 in the amount of 50 to 500 mg, 50 to 400 mg, 50 to 300 mg, 100 to 400 mg, 100 to 300 mg, 50 to 200 mg, or 100 to 200 mg, preferably 50 to 300 mg, more preferably 50 to 200 mg, based on the free form.

The medicament or pharmaceutical composition according to one embodiment of the present invention may be formulated using a pharmaceutically acceptable carrier and/or excipient according to a method that a person having ordinary skill in the art could easily carry out, thereby to be prepared in a unit dose form or to be contained in a multi-dose container. The above formulation may be a solution in oil or an aqueous medium, a suspension or an emulsion (emulsified solution), an extract, a powder, granules, a tablet, or a capsule, and may further include a dispersing or stabilizing agent. In addition, the pharmaceutical composition may be administered in the form of suppositories, sprays, ointments, creams, gels, inhalants or skin patches. The pharmaceutical composition may also be prepared for mammalian administration, more preferably for human administration.

Pharmaceutically acceptable carriers may be solid or liquid, and may be one or more selected from fillers, antioxidants, buffers, bacteriostats, dispersants, adsorbents, surfactants, binders, preservatives, disintegrants, sweeteners, flavors, glidants, release-controlling agents, wetting agents, stabilizers, suspending agents, and lubricants. In addition, the pharmaceutically acceptable carriers may be selected from saline, sterile water, Ringer's solution, buffered saline, dextrose solution, maltodextrin solution, glycerol, ethanol and mixtures thereof.

In one embodiment, suitable fillers include, but are not limited to, sugar (e.g., dextrose, sucrose, maltose and lactose), starch (e.g., corn starch), sugar alcohol (e.g., mannitol, sorbitol, maltitol, erythritol and xylitol), starch hydrolysate (e.g., dextrin and maltodextrin), cellulose or cellulose derivatives (e.g., microcrystalline cellulose) or mixtures thereof.

In one embodiment, suitable binders include, but are not limited to, povidone, copovidone, methylcellulose, hydroxypropylmethylcellulose, hydroxypropylcellulose, hydroxyethylcellulose, gelatin, gum, sucrose, starch or mixtures thereof.

In one embodiment, suitable preservatives include, but are not limited to, benzoic acid, sodium benzoate, benzyl alcohol, butylated hydroxyanisole, butylated hydroxytoluene, chlorbutol, gallate, hydroxybenzoate, EDTA or mixtures thereof.

In one embodiment, suitable disintegrants include, but are not limited to, sodium starch glycolate, cross-linked polyvinylpyrrolidone, cross-linked carboxymethylcellulose, starch, microcrystalline cellulose or mixtures thereof.

In one embodiment, suitable sweeteners include, but are not limited to, sucralose, saccharin, sodium saccharin, potassium saccharin, calcium saccharin, acesulfame potassium or sodium cyclamate, mannitol, fructose, sucrose, maltose or mixtures thereof.

In one embodiment, suitable glidants include, but are not limited to, silica, colloidal silicon dioxide, talc and the like.

In one embodiment, suitable lubricants include, but are not limited to, long chain fatty acids and salts thereof, such as magnesium stearate and stearic acid, talc, glyceride wax or mixtures thereof.

As used herein, the terms "prevent," "preventing" and "prevention" refer to reducing or eliminating the likelihood of a disease.

As used herein, the terms "alleviate," "alleviating" and "alleviation" refer to ameliorating a disease and/or its accompanying symptoms altogether or in part.

As used herein, the terms "treat," "treating" and "treatment" refer to eliminating a disease and/or its accompanying symptoms altogether or in part.

As used herein, the term "subject" refers to an animal that is the object of therapy, observation or experiment, preferably a mammal (such as primates (e.g., a human), cattle, sheep, goats, horses, dogs, cats, rabbits, rats, mice, etc.), most preferably a human.

As used herein, the term "therapeutically effective amount" refers to the amount of active compound or pharmaceutical formulation that elicits a biological or medical response in the system, animal or human, including alleviation of the symptoms of the disease or disorder to be treated, wherein said amount is sought by a researcher, veterinarian, doctor (physician) or other clinician.

As used herein, the term "composition" encompasses a product that contains a specified amount of a particular ingredient and any product that results directly or indirectly from a combination of specified amounts of particular ingredients.

Effect of the Invention

The medicament and the pharmaceutical composition according to the present invention can effectively treat and prevent pruritus without side effects compared to existing therapeutic agents.

DETAILED DESCRIPTION

Hereinafter, the present invention will be explained in more detail through working examples. However, the following working examples are only intended to illustrate one or more embodiments and are not intended to limit the scope of the invention.

Preparation Example: Synthesis of Carbamic Acid (R)-1-(2-chlorophenyl)-2-tetrazol-2-yl)ethyl Ester Carbamic acid (R)-1-(2-chlorophenyl)-2-tetrazol-2-yl) ethyl ester (hereinafter referred to as "the test compound") was prepared according to the method described in Preparation Example 50 of PCT Publication No. WO 2010/150946.

Example 1: Experiment of Pruritus Inhibiting Effect in Acute Pruritus Animal Model Induced by Intradermal Administration of Serotonin Experimental Animals Mature male rats (Sprague-Dawley, 200 to 230 g) were used. The experimental animals were maintained at a light-and-darkness cycle of 12 hours (illuminated from 7 pm to 7 am), a temperature of 22 to 25° C., a relative humidity of 40 to 60%, and free access to water and food. The animals were randomly divided into three groups as follows:

Eight (8) rats as a control group, orally administered with 30% PEG400 as a vehicle at a dose of 5 ml/kg Eight (8) rats, orally administered with the test compound at a dose of 10 mg/kg (5 ml/kg)

Eight (8) rats, orally administered with the test compound at a dose of 30 mg/kg (5 ml/kg)

Induction of Acute Pruritus

On the day before the experiment, the skin fur on the right scapula of the rats was shaved to an area of about 2 cm square. On the day of the experiment, serotonin hydrochloride was dissolved in 0.9% physiological saline at a concentration of 4 mg/ml. The rats were placed in an acrylic box (20×30×20 cm) and adapted for 15 minutes in a quiet area, followed by intradermal administration of the dissolved serotonin in 50 μl per rat on the shaved area (Thomsen et al, Scratch induction in the rat by intradermal serotonin: a model for pruritus, Acta Derm Venereol, 2001).

Measurement of Scratching Reactions

The number of scratching behaviors was observed for 30 minutes immediately after serotonin administration, and one continuous scratching reaction was counted as one scratching reaction. Only when the rats scratched body parts within 5 cm square around the skin area where serotonin was administered, it was judged to be a valid scratching reaction.

Administration

The test compound was orally administered to the rats at a dose of 10 mg/kg (5 ml/kg) and 30 mg/kg (5 ml/kg) 1 hour before intradermal administration of serotonin.

Statistics

The effect of the compound was expressed as mean±standard error, and statistical significance was recognized when data had a difference of $p<0.05$ using one-way ANOVA and Dunnett's test.

Figure 1:
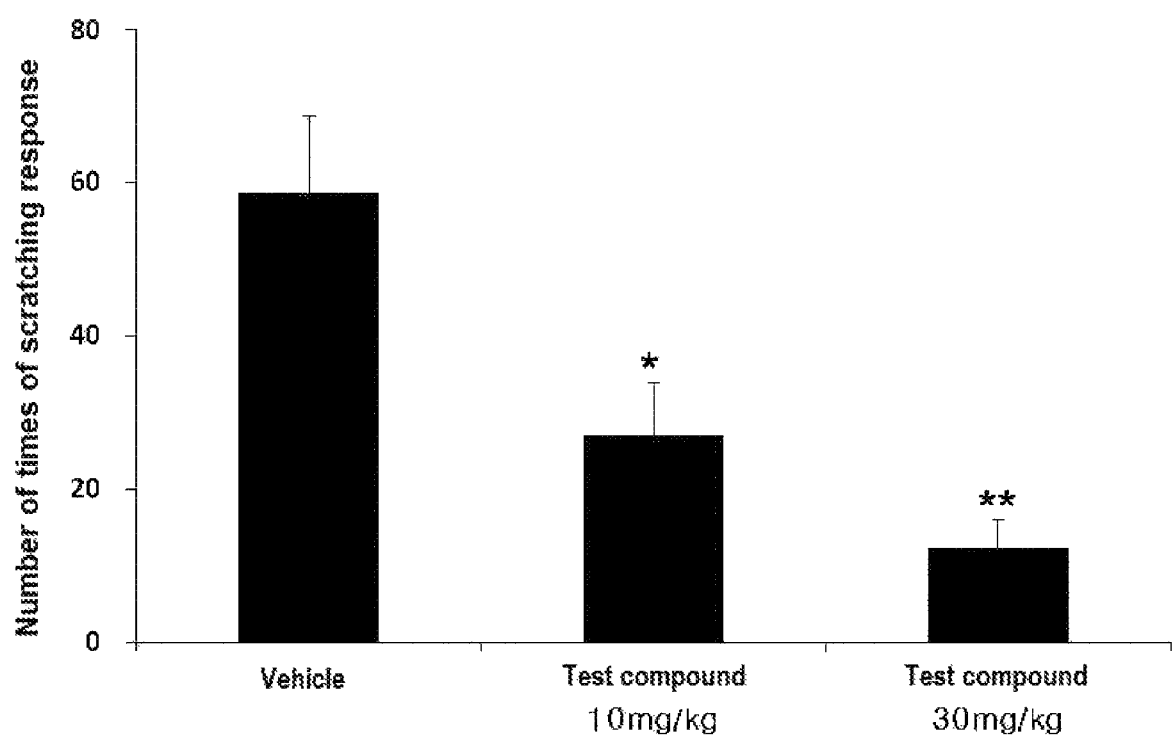
FIG. 1 shows the effect of carbamic acid (R)-1-(2-chlorophenyl)-2-tetrazol-2-yl)ethyl ester prepared in the Preparation Example ("the test compound") to reduce the number of scratching reactions compared to the control group (vehicle) after administering to rats with acute pruritus that has been induced by intradermal administration of serotonin.

As can be seen from FIG. 1, when the test compound was orally administered at a dose of 10 mg/kg and 30 mg/kg, it was confirmed that the acute pruritus induced by intradermal administration of serotonin was statistically significantly inhibited compared to the control group. The reduction of these itching responses was observed as dose-dependent.

As described above, the test compound showed a statistically significant effect in serotonin-induced acute pruritus animal models.

Example 2: Experiment of Pruritus Inhibiting Effect in Chronic Pruritus Animal Model Induced by Subcutaneous Administration of Capsaicin Immediately after Birth Experimental Animals Baby rats within 48 hours after birth (Sprague-Dawley, 7 to 10 g) were obtained together with the mother rats, and were used. The experimental animals were maintained at a light-and-darkness cycle of 12 hours (illuminated from 7 pm to 7 am), a temperature of 22 to 25° C., a relative humidity of 40 to 60%, and free access to water and food. Until the 21st day after birth, the baby rats were bred together with the mother rats and allowed to drink the mother's milk. After the 21st day, the baby rats were kept off the milk and separated from the mother rats. The animals were randomly divided into two groups as follows:

Seven (7) rats as a control group, orally administered with 30% PEG400 as a vehicle at a dose of 5 ml/kg Seven (7) rats, orally administered with the test compound at a dose of 30 mg/kg (5 ml/kg)

Induction of Chronic Pruritus

Capsaicin was dissolved in vehicle (10% Tween-80 and 10% ethanol in 0.9% saline) at a concentration of 50 mg/kg and administered subcutaneously on the right hip of the baby rats within 48 hours after birth in 10 μl per rat (Back et al, Chronically relapsing pruritic dermatitis in the rats treated as neonate with capsaicin; a potential rat model of human atopic dermatitis, Journal of Derm Science, 2012).

Measurement of Scratching Reactions

On the third week after capsaicin administration, the animals were placed in an acrylic box (20×30×20 cm), adapted for 30 minutes in a quiet area, and then observed for the number of scratching behaviors for 1 hour. One continuous scratching reaction was counted as one scratching reaction. Scratching any part of the body with no restriction to specific body parts was judged to be a valid scratching reaction.

Administration

The test compound was orally administered to the rats at a dose of 30 mg/kg (5 ml/kg) 1 hour before the measurement of scratching reactions.

Statistics

The effect of the compound was expressed as mean±standard error, and statistical significance was recognized when data had a difference of $p<0.05$ using one-way ANOVA and Dunnett's test.

Figure 2:
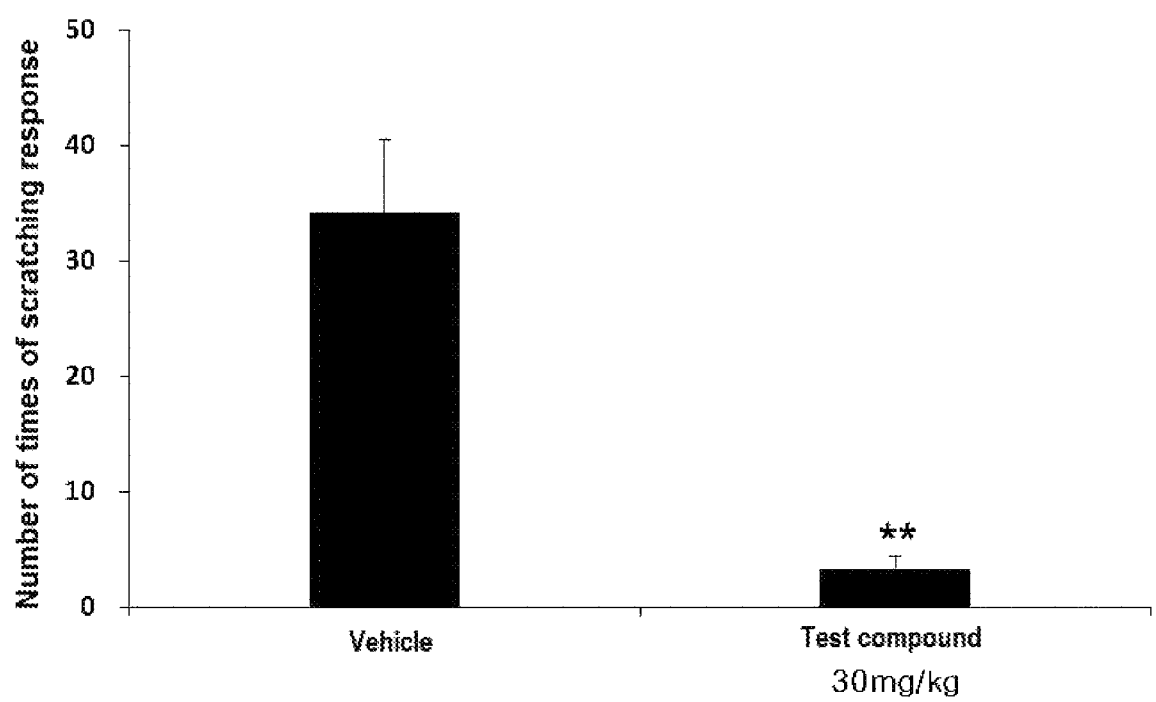
FIG. 2 shows the effect of the test compound to reduce the number of scratching reactions compared to the control group (vehicle) after administering to rats with chronic pruritus that has been induced by subcutaneous administration of capsaicin immediately after birth.

As can be seen from FIG. 2, when the test compound was orally administered at a dose of 30 mg/kg, it was confirmed that the chronic pruritus induced by administration of capsaicin immediately after birth was statistically significantly inhibited compared to the control group.

As described above, the test compound showed a statistically significant effect in capsaicin-induced chronic pruritus animal models.

From the above results, it was confirmed that the test compound showed a significant effect in the acute and chronic pruritus disease models and thus could be effectively used as a drug for the treatment of pruritus.

What is claimed is:

1. A method for alleviating or treating pruritus in a subject, comprising administering to the subject a therapeutically effective amount of a carbamate compound of the following Formula 1, or a pharmaceutically acceptable salt, thereof:

[Formula 1]

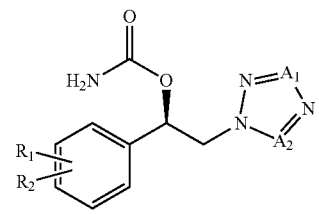

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

2. The method according to claim 1, wherein $R_1$ and $R_2$ are each independently selected from the group consisting of hydrogen, halogen and $C_1$-$C_8$ alkyl.

3. The method according to claim 1, wherein the carbamate compound of Formula 1 is carbamic acid (R)-1-(2-chlorophenyl)-2-tetrazol-2-yl)ethyl ester of the following Formula 2:

[Formula 2]

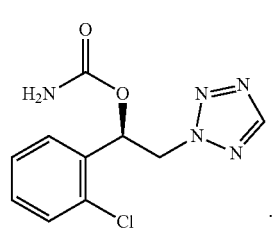

4. The method according to claim 1, wherein the pruritus is an acute pruritus.

5. The method according to claim 4, wherein the acute pruritus is an acute pruritus due to skin disease.

6. The method according to claim 4, wherein the acute pruritus is caused by one or more selected from Erythema multiforme, Urticaria caused by external allergy-inducing substances and Acute eczematous dermatitis.

7. The method according to claim 1, wherein the pruritus is a chronic pruritus.

8. The method according to claim 7, wherein the chronic pruritus is one or more selected from chronic pruritus caused by skin diseases, pruritus caused by systemic diseases, pruritus caused by neuropathies, pruritus caused by psychotic diseases and mixed-type pruritus thereof.

9. The method according to claim 8, wherein the chronic pruritus caused by skin diseases is caused by one or more selected from Psoriasis, Atopic dermatitis, Contact dermatitis, Urticaria, Dry skin, Prurigo, Scabies mite, Insect bite, Mycotic, bacterial and viral infections, Folliculitis, Pediculosis, Bullous dermatoses, Dermatitis herpetiform is Duhring, Bullous pemphigoid, Dermatomyositis, Darier's disease, Hailey-Hailey disease, Ichthyosis, Sjogren-Larsson syndrome, Epidermolysis bullosa pruriginosa, Polymorphic eruption of pregnancy, Pemphigoid gestationis, Prurigo gestationis, Cutaneous T-cell and B-cell lymphoma and Leukemic infiltrates of the skin;

the pruritus caused by systemic diseases is caused by one or more selected from Chronic liver disease, Chronic renal failure, Diabetes mellitus, Biliary Atresia, Uremia, Hyperthyroidism, Malabsorption, Perimenopausal pruritus, HIV infection, Helm inthiasis, Iron deficiency, Polycythaemia vera, Hodgkin's disease, Non-Hodgkin's lymphoma, Plasmocytoma, Solid tumours of the cervix, prostate or colon, Carcinoid syndrome, Pruritus gravidarum, and administration of drugs;

the pruritus caused by neuropathies is caused by one or more selected from Post-herpetic pruritus, Notalgia paresthetica, Brachioradial pruritus, Post-cerebrovascular accident (CVA) pruritus, Multiple sclerosis, Neoplasms, Abscesses, Cerebral or spinal infarcts, Vulvodynia and Small fiber neuropathy; and the pruritus caused by psychotic diseases is caused by one or more selected from Delusions of parasitosis, Stress, Depression, Anxiety disorders, Obsessive-compulsive disorders, Schizophrenia, Tactile hallucinosis and Systemic fatigue.

10. The method according to claim 1, wherein the subject is a mammal.

11. The method according to claim 10, wherein the mammal is a human.

12. The method according to claim 1, wherein the therapeutically effective amount of the carbamate compound of Formula 1 is 50 mg to 500 mg based on the free form.

\* \* \* \* \*